United States Patent [19]

Brendl et al.

[11] Patent Number: 4,579,323
[45] Date of Patent: Apr. 1, 1986

[54] X-RAY DIAGNOSTIC DEVICE HAVING A TILTABLE TABLE

[75] Inventors: Rüdolf Brendl; Alfred Hahn, both of Erlangen; Karl Weiss, Buckenhof, all of Fed. Rep. of Germany

[73] Assignee: Siemens Aktiengesellschaft, Berlin & Munich, Fed. Rep. of Germany

[21] Appl. No.: 666,281

[22] Filed: Oct. 29, 1984

[30] Foreign Application Priority Data

Dec. 5, 1983 [DE] Fed. Rep. of Germany ....... 3343877

[51] Int. Cl.⁴ ............................................. A61G 13/00
[52] U.S. Cl. .................................................... 269/323
[58] Field of Search ................. 269/322, 323; 378/209; 108/4–8

[56] References Cited

U.S. PATENT DOCUMENTS 2,534,623 12/1950 Pitts et al.
3,525,308 8/1970 Koopmans.

OTHER PUBLICATIONS

Sales brochure entitled, "Pantoskop 4 mit Explorator 35", Siemens Corporation, date unknown.

Primary Examiner—Robert C. Watson
Attorney, Agent, or Firm—Hill, Van Santen, Steadman & Simpson

[57] ABSTRACT

An improved x-ray diagnostic apparatus having a table mounted on a table support and being tiltable on a support base to positions on each side from a horizontal position with one of the side positions being through 90° characterized by a drive arrangement including a curved drive track on the table support engaged by drive wheels mounted on the support base and a guide arrangement including two spaced guide rails on the table support receiving guide pins or members of the support base when the table is in the horizontal position. When the table moves from the horizontal position, the guide rail of the upper end of the table disengages from its respective guide pin so that the guide rail at the lower end coacting with its guide pin and the support provided by the drive arrangement coact to maintain the lower end above the floor level. Preferably, the drive arrangement also includes a support arrangement having a curved support track engaging a support roller so that only tangential forces are applied between the drive wheel and drive track.

10 Claims, 4 Drawing Figures

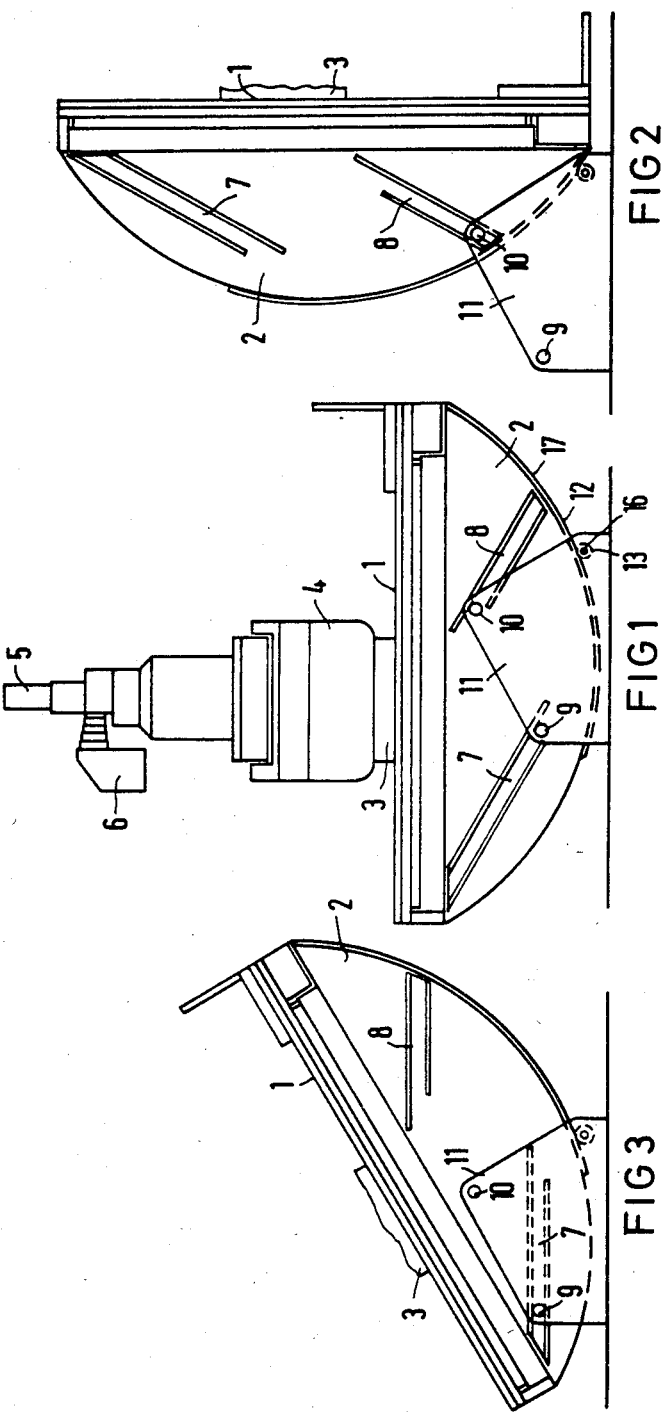

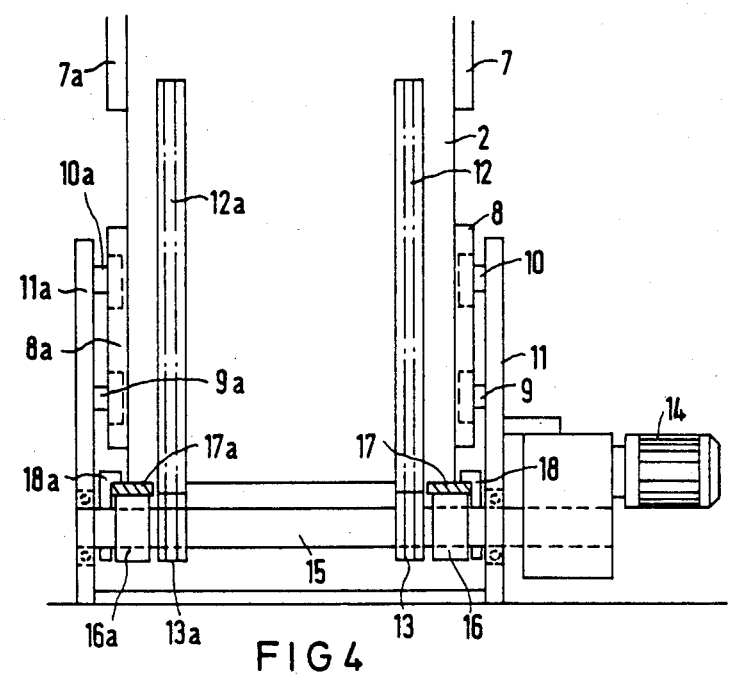

X-RAY DIAGNOSTIC DEVICE HAVING A TILTABLE TABLE

BACKGROUND OF THE INVENTION

The present invention is directed to an x-ray diagnostic apparatus having a table support with a table mounted with a table surface thereon and the table support is tiltable on a base to positions on each side from a horizontal position with one of the side positions having the table surface tilted through an angle of 90° so that the table surface is approximately in a vertical position. To tilt the table on the support base, a drive arrangement which includes one or more curved drive tracks which are part of a circular arc are provided on the table support and coact with drive wheels or gears which are positioned on the support base and are rotated by a drive motor. To help guide the table support during tilting, two rectilinear guide rails or tracks are arranged on the table support.

In the case of known x-ray diagnostic apparatuses of the above-mentioned type, the tilting table is guided by various types of guide means, for example, cam guides or gear guides in such a fashion that the required table positions, such as the horizontal position with the top or table surface lying in the horizontal plane, one side position with the table top being tilted through 90° to be substantially in a vertical plane and another side position, for example, wherein the table top is in a plane extending at 30° to a horizontal plane, can be obtained. The known guide arrangements, which in particular effect the longitudinal displacement of the tilting table in its support base during a setting up from the horizontal position are constructed in a relatively complicated fashion.

SUMMARY OF THE INVENTION

The present invention has an object which consists in providing an x-ray diagnostic apparatus, which has a table that can be tilted from a horizontal position to positions on each side with one of the side positions having the table surface being in a vertical plane, with a structural outlay necessary for tilting the table being substantially reduced as compared with the structure known in the state of the art. Thus, a stable table is guaranteed in all positions. In particular, the tilting table in addition to its vertical and horizontal positions, is additionally provided with a head-low-position in which it is tilted approximately 30° relative to the horizontal line.

The above objects are obtained in an improvement in an x-ray diagnostic apparatus comprising a table being mounted on a table support and being tiltable on a base support to positions on each side from a horizontal position with one side position being through 90°, said apparatus including drive means comprising at least one curved drive track being positioned on the table support opposite the table surface and being engaged by a drive wheel mounted for rotation on the support base, said apparatus also having guide means including two rectilinear guide rails. The improvement is that the guide means includes a stationary guide member or pin associated with each of the guide rails of the table support, said guide members being positioned in the base support and the guide rails being positioned in the table support so that each rail is engaged by its associated guide member when the table support is in the horizontal position and when the table support is tilted, one of the guide members disengages from its associated rail and the other guide member while engaged with its rail coacts with the drive means to maintain the lower end of the tilted table above the floor level.

In the preferred embodiment, the guide rails, the guide pins, the curved drive track and the drive wheels are arranged in spaced pairs disposed along the sides of the table support. In addition, the drive means in addition to the drive track includes curved support tracks having the same curvature which is engaged by a support roller. These support tracks project laterally somewhat beyond the edge of the table support and are engaged by a safety hook arrangement which are positioned outside of the sides of the table support and are secured on the support base. Preferably, the guide rails are formed of two parallel members which receive the guide pin or element which is preferably a roller and the upper member of each pair is longer than the lower member so that it is engaged when the table support is in the horizontal position but enables the guide pin of the upper end to become disengaged as the table is tilted.

The object underlying the invention is solved by virtue of the fact that the two stationary guide pins engaged in the guide rails while the table is in the horizontal position, are so designed and directed that during movement of the tilting table from the horizontal position the guide rail or track associated with the upper end of the tilted table will disengage from its associated guide pin while the lower end of the table support is raised to such an extent that it lies above the floor level. In the inventive x-ray table, the table support with the tilting table while in the horizontal position rests on the two guide pins. If it is tilted from the horizontal position toward one side, one of the guide pins will leave that associated guide rail while the other guide pin effects, via its guide rail, such a movement of the table support during tilting that the table support can assume the desired tilted position without striking or contacting the floor. The guide means are very simply constructed and consist of only rectilinear guide rails, the guide pins and the drive means. In order to relieve the drive wheels and the drive track of the bearing loads or reaction forces, it is desirable to provide an additional support roller which is mounted on the shaft for the drive wheel and which support roller engages a curved support track and positioned to lie in the same curved surface as the drive track. In this case, the support consisting of the support roller and the support track assumes a radial support force for the table support so that only tangential forces are to be transmitted through the drive track which is expediently designed in the form of a chain and the drive wheel which is designed in this instance in the form of a sprocket wheel.

A particularly stable guidance is guaranteed if each side of the apparatus is provided with a symmetrical arrangement consisting of one drive track, one drive wheel, one support track, one support roller, two guide rails and two guide pins. In order that the table support will not be inadvertently raised from its support surfaces, the support tracks can laterally protrude somewhat beyond the table support and can be engaged by safety hooks which are stationarily arranged on both sides of the support base.

BRIEF DESCRIPTION OF THE DRAWINGS

FIG. 1 is a schematic side view of an x-ray diagnostic apparatus according to the present invention while in a horizontal position;

FIG. 2 is a schematic side view of the x-ray diagnostic apparatus of FIG. 1 tilted to a vertical position;

FIG. 3 is a schematic side view of the x-ray diagnostic apparatus of FIG. 1 when tilted in the opposite direction to a tilted position; and FIG. 4 is an end view with portions in cross-section for purposes of illustration with the table being in a partial tilted position between that illustrated in FIGS. 1 and 2.

DESCRIPTION OF THE PREFERRED EMBODIMENTS

The principles of the present invention are particularly useful in apparatus generally illustrated in FIGS. 1-3 which has a tiltable table 1 having a table surface which is mounted on a table support 2 so as to be longitudinally displaceable in a support base by motor means which includes the motor 14 (FIG. 4). An x-ray tube (not shown) is positioned beneath the surface of the table 1, and the x-ray tube is secured to a support 3, which also supports above the surface of the tilting table 1 an x-ray image intensifier 4 with a post-connection television camera 5 and a sheet film camera 6. In the horizontal position as illustrated in FIG. 1, the table support 2 has guide means comprising rectilinear guide rails 7 and 8 which rest on guide pins 9 and 10 of a side member 11 of a support base.

The table support 2 is provided with curved drive track 12 and 12a with one adjacent each side (FIG. 4). Each of these drive tracks, as best illustrated in FIG. 1, is a curved track which is a segment of a circle. Drive wheels 13 and 13a are mounted on a shaft 15 (FIG. 4) which is rotated by a motor 14 which is connected to the drive shaft by a gear reduction device. Each of the drive tracks 12 and 12a are designed in the form of a chain and each of the wheels 13 and 13a is a sprocket gear.

As illustrated in FIG. 4, the guide rails 7 and 8 are arranged in pairs so that there are guide rails 7 and 8 on one side of the table support 2 and rails 7a and 8a on the other side. In a similar manner, the support base has two side members 11 and 11a which position guide pins or members 9 and 10 on the side 11 and 9a and 10a on the side 11a. In addition, as illustrated, the shaft 15 besides having the drive wheels 13 and 13a also has support rollers 16 and 16a. The support rollers 16 and 16a engage curved support tracks 17 and 17a which are mounted adjacent the drive tracks 12 and 12a and have the same degree of curvature so that the rollers 16 and 16a and their respective support tracks 17 and 17a support the table 2 as it is being shifted through the various positions.

If the table 1 and the table support 2 is in the position illustrated in FIG. 1, then the table support is supported with the guide rails 7 and 7a engaged on guide pins 9 and 9a and the guide rails 8 and 8a engaged on the guide rails 10 and 10a and the support rollers 16 and 16a on the support tracks 17 and 17a. When being moved to a vertical position such as illustrated in FIG. 2, the drive motor 14 is switched on and will rotate the shaft 15 and hence the drive wheels 13 and 13a. The support table as it begins to tilt toward the vertical position will have the guide pins 9 and 9a go out of engagement with the rails 7 and 7a. Then the support table 2 will only rest on the contact between the guide rails 8 and 8a on the guide pins 10 and 10a and on the support tracks 17 and 17a on the support rollers 16 and 16a. Through the guidance of the pins 10 and 10a and the guide rails 8 and 8a, it is possible that the tilting table can be set up into the position illustrated in FIG. 2 without the lower end striking the floor.

If the table 1 is to be pivoted from its horizontal position as illustrated in FIG. 1 in a counterclockwise direction, then in an analogous fashion, the guide pins 10 and 10a are disengaged from the guide rails 8 and 8a and the guidance proceeds by means of the guide pins 9 and 9a and the guide rails 7 and 7a as illustrated in FIG. 3. To accomplish this movement, the drive wheels 13 and 13a rotate opposite to their rotation in the case of moving to the table to the vertical position. The table support 2 is thus pivoted in a counterclockwise direction into the head-low-position illustrated in FIG. 3 in which the surface of the table 1 forms an angle with the plane of the floor which is approximately 30°.

During movement of the table 1 from its horizontal position of FIG. 1 into either of the side positions of FIG. 2 or 3, one of the pair of guide pins 9 and 9a or 10 and 10a leaves its respective guide tracks 7 and 7a or 8 and 8a and the end of the apparatus which is in the greater proximity of the floor, respectively, is raised to such an extent that it will lie above the floor level. It is noted that the table support 2 is supported by the support rollers 16 and 16a on the support tracks 17 and 17a and the particular pair of guide pins and guide rails associated with the lower end.

In order to avoid sliding friction on the guide rails such as 7, 7a, 8 and 8a, the guide pins 9, 9a, 10 and 10a are expediently formed as anti-friction bearings or rollers. For a jolt-free, secure movement of the table support 2, each of the drive tracks 12 and 12a can also consist of several parallel chains into whch one drive wheel on a shaft 15 is engaged, respectively. In this case, it is expedient to provide three parallel extending chains for each drive track with the chains being directly adjacent one another such as indicated in FIG. 4. These three chains will receive three sprockets.

From FIG. 4, it is apparent that the support tracks 17 and 17a project laterally somewhat beyond the sides of the table support 2 and are embraced by safety hooks 18 and 18a which are stationarily arranged on both sides of the support table. These safety hooks prevent an inadvertent raising of the table support 2 from the support rollers 16 and 16a. The safety hooks 18 and 18a as well as the drive motor 14, are not illustrated in FIGS. 1-3 for reasons of clarity.

As illustrated in FIGS. 1, 2 and 3, it is noted that each of the tracks 7 and 8 extend parallel to each other and are composed of two members with the upper member or the member closer to the table 1 being longer than the lower member or the member closer to the track 12. These two members for each of the tracks extend on opposite sides of the pin and coact to guide the pin during movement of the table between positions. It should be noted that the tracks 7a and 8a are also constructed in a similar manner and extend parallel to each other.

Although various minor modifications may be suggested by those versed in the art, it should be understood that we wish to embody within the scope of the patent granted hereon, all such modifications as reasonably and properly come within the scope of our contribution to the art.

We claim:

1. In an x-ray diagnostic apparatus comprising a table being mounted on a table support and being tiltable on a support base to positions on each side from a horizontal position with one side position being through 90°, said apparatus having drive means including the table support having at least one curved drive track engaged by a drive wheel mounted for rotation on the support base, said apparatus having guide means including two rectilinear guide rails disposed on the table support, the improvements comprising the guide means including a stationary guide member associated with each of the guide rails and being mounted on the support base, said guide members being positioned on the support base and the guide rails being positioned on the table support so that each rail is engaged by its associated guide member when the table support is in the horizontal position and when the table support is tilted one guide member disengages from its associated rail and the other guide member while engaging with its rail coacts with the drive means to maintain the lower end of the tilted table above the floor level.

2. In an x-ray diagnostic apparatus according to claim 1, wherein the drive means further include a support roller mounted on a shaft of the drive wheel and a curved support track mounted adjacent to the drive track and having the same curvature so that the support roller and support track carry the radial force and only the tangential force acts between the drive wheel and drive track.

3. In an x-ray diagnostic apparatus according to claim 2, wherein the support track is engaged by a safety hook stationarily secured to the support base to prevent intermittent disengagement between the drive wheel and drive track.

4. In an x-ray diagnostic apparatus according to claim 1, wherein the drive means includes a pair of drive tracks disposed along each side of the table support, and a pair of drive wheels for engaging the pair of drive tracks, wherein the support base has a pair of side members arranged to receive the table support therebetween, said table support having a pair of guide rails on each side and each of said side members having a pair of the guide members arranged to engage the pair of guide rails disposed on the side of the table support.

5. In an x-ray diagnostic apparatus according to claim 4, wherein the drive means includes support means comprising a curved support track mounted on the table support adjacent to each of the drive tracks, said support track having the same curvature as the drive track and being engaged by a support roller mounted on a shaft with the drive wheels.

6. In an x-ray diagnostic apparatus according to claim 5, wherein each of the support tracks projects laterally outward of the sides of the table support and the apparatus includes safety hooks stationarily arranged on the support base engaging the projecting edge of each of the support tracks.

7. An x-ray diagnostic apparatus having a table surface being tilted to positions on each side from a horizontal position with one side position having the table surface being approximately vertical, said apparatus comprising a table support, a table with a table surface being mounted on the table support, a support base, drive means for tilting the table and the table support on the support base including at least one curved drive track positioned on the table support on a side opposite the table surface and a drive wheel mounted for rotation in the support base engaging the drive track, guide means including a pair of rectilinear guide tracks disposed on the table support and coacting with guide members positioned on the support base, said guide tracks and guide members being positioned so that when the table is in a horizontal position, the guide tracks are engaged by the respective guide members and when the table is tilted from the horizontal position by the drive means, the guide track at the elevated end becomes disengaged from the associated guide member and the guide track and associated guide member at the lower end of the table and the drive means coact to support the table and table support with the lower end being maintained above the floor level.

8. An x-ray diagnostic apparatus according to claim 7, wherein the support base includes two side members with the table support extending therebetween, said table support having a pair of guide rails on each side facing the side members, each of said side members having two guide members engageable with respective guide tracks on the side of the table support, said drive means including a pair of drive tracks arranged adjacent the sides of the table support and being engaged by a pair of drive wheels.

9. An x-ray diagnostic apparatus according to claim 9, wherein the drive means includes support means comprising a pair of curved support tracks arranged adjacent to the pair of drive tracks and having the same curvature as the drive tracks, and support rollers mounted on the drive shaft for the drive wheel engaging the support tracks so that only tangential forces are applied between the drive tracks and drive wheels.

10. An x-ray diagnostic apparatus according to claim 9, wherein the support tracks are disposed outwardly of the drive tracks and protrude laterally beyond the side of the table support, said device including safety hooks mounted on the support base engaging the protruding edges of the support tracks.

* * * * *